(12) United States Patent
Tashiro

(10) Patent No.: US 8,764,659 B2
(45) Date of Patent: Jul. 1, 2014

(54) ULTRASOUND IMAGE GENERATING APPARATUS

(75) Inventor: Rika Tashiro, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 124 days.

(21) Appl. No.: 13/197,031

(22) Filed: Aug. 3, 2011

(65) Prior Publication Data

US 2012/0035477 A1 Feb. 9, 2012

(30) Foreign Application Priority Data

Aug. 3, 2010 (JP) ................................ 2010-174635

(51) Int. Cl.
*A61B 8/13* (2006.01)

(52) U.S. Cl.
USPC ............ 600/439; 600/443; 600/447; 600/437

(58) Field of Classification Search
None
See application file for complete search history.

(56) References Cited

U.S. PATENT DOCUMENTS

| | | | |
|---|---|---|---|
| 6,315,723 B1 * | 11/2001 | Robinson et al. ............. | 600/443 |
| 6,432,056 B1 | 8/2002 | Cooley et al. | |
| 6,544,179 B1 | 4/2003 | Schmiesing et al. | |
| 8,460,192 B2 | 6/2013 | Yoshiara et al. | |
| 2007/0197916 A1 | 8/2007 | Kawagishi et al. | |
| 2009/0326377 A1 | 12/2009 | Hirama | |
| 2010/0036255 A1 | 2/2010 | Itani | |

FOREIGN PATENT DOCUMENTS

| | | |
|---|---|---|
| CN | 101006932 A | 8/2007 |
| CN | 101548896 A | 10/2009 |
| CN | 101642379 A | 2/2010 |
| JP | 63277046 A | 11/1988 |
| JP | 03139339 A | 6/1991 |
| JP | 2001269339 A | 10/2001 |
| JP | 2002058671 A | 2/2002 |
| JP | 2003511173 A | 3/2003 |
| JP | 2004208859 A | 7/2004 |
| JP | 2005511235 A | 4/2005 |
| JP | 2006320378 A | 11/2006 |
| JP | 2007301122 A | 11/2007 |
| JP | 2008142413 A | 6/2008 |
| JP | 2008-188178 A | 8/2008 |
| JP | 2010094220 A | 4/2010 |

OTHER PUBLICATIONS

Notification of Reasons for Refusal, dispatched Oct. 15, 2013, issued in corresponding JP Application No. 2010-174635, 6 pages in English and Japanese.

Notification of Reasons for Refusal, dated Jan. 14, 2014, issued in corresponding JP Application No. 2010-174635, 8 pages in English and Japanese.

The First Office Action, dated Mar. 4, 2014, issued in corresponding CN Application No. 201110220630.6, 22 pages in English and Chinese.

* cited by examiner

*Primary Examiner* — Long V. Le
*Assistant Examiner* — Farshad Negarestan
(74) *Attorney, Agent, or Firm* — Sughrue Mion, PLLC

(57) ABSTRACT

An ultrasound image having a good image quality is generated in the neighborhood of a puncture needle without lowering the image quality of the whole ultrasound image. A first echo signal received by transmitting first ultrasonic waves focused on an imaging target position and a second echo signal received by transmitting second ultrasonic waves having the depth of the focal point positioned at a uniform position are obtained, the weights of the first echo signal and the second echo signal are determined according to the focal point positions of the respective ultrasonic waves, and weighted addition is performed to generate a corrected image.

10 Claims, 13 Drawing Sheets

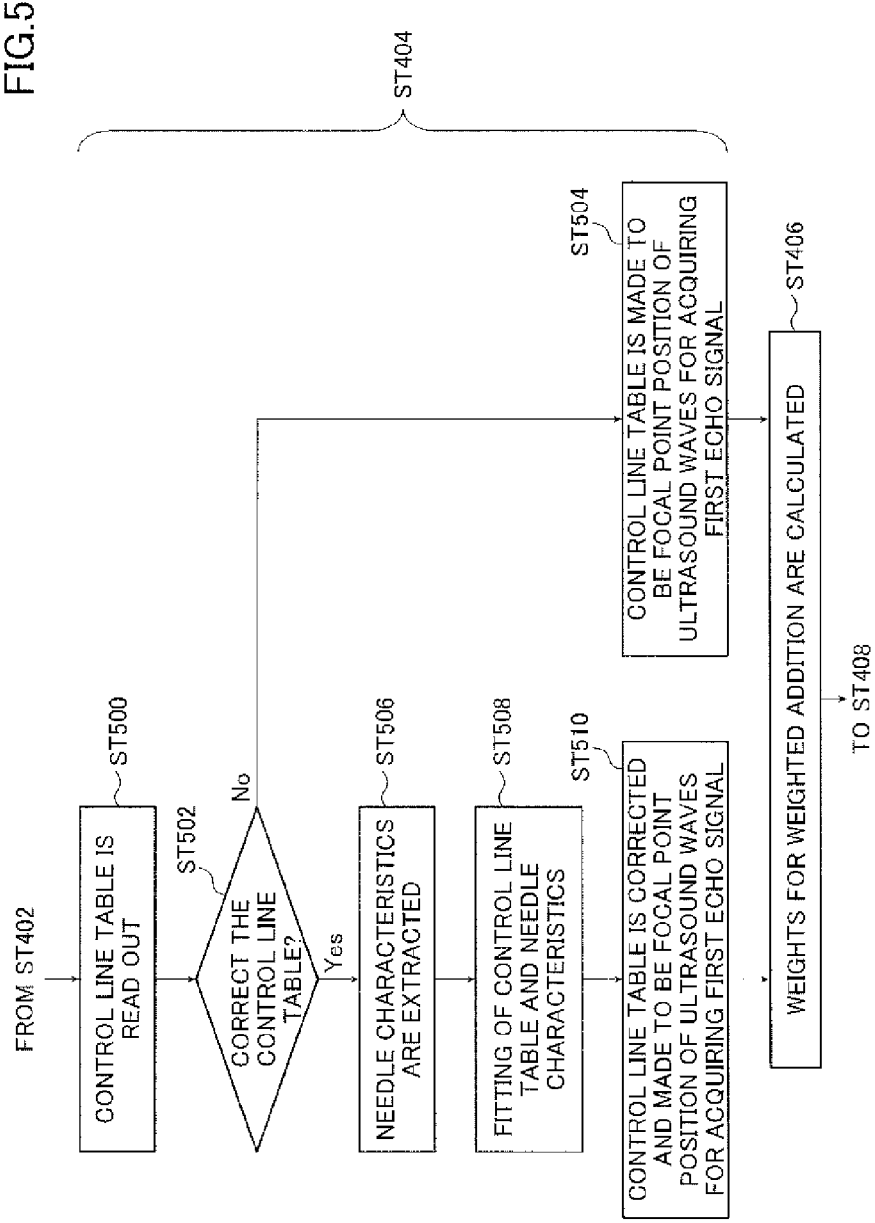

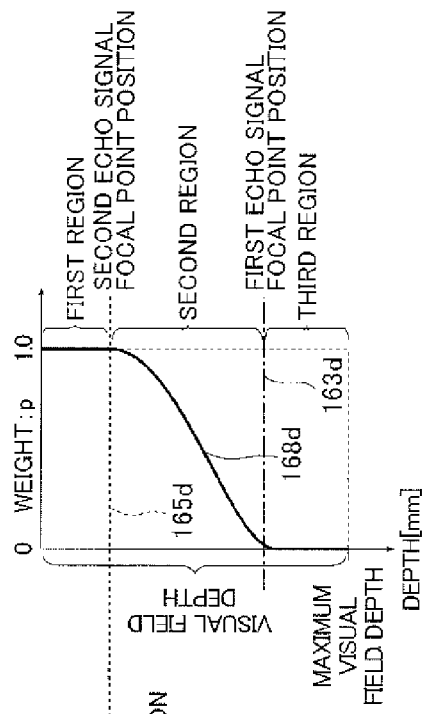
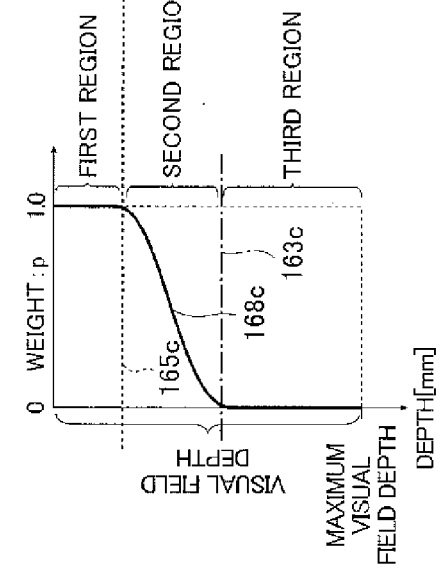

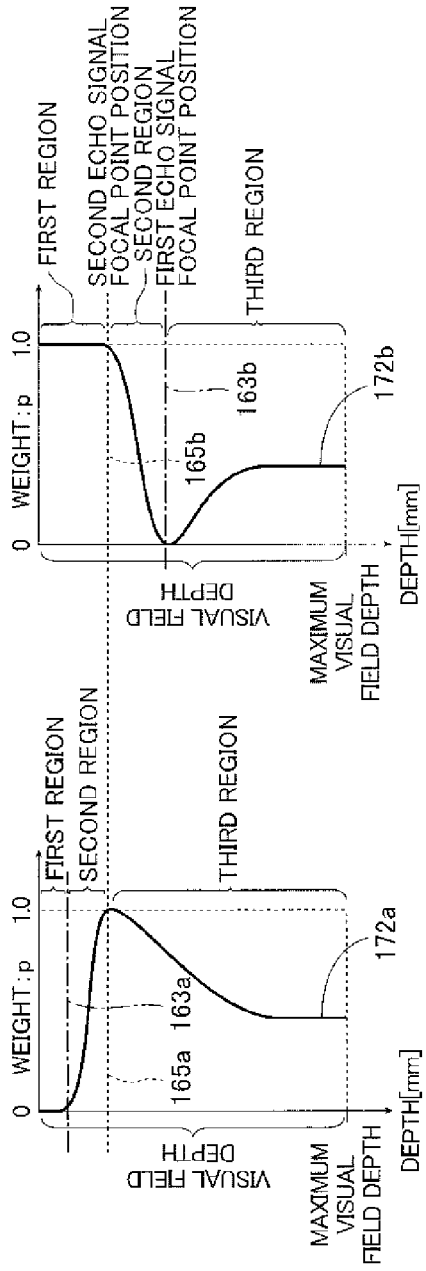

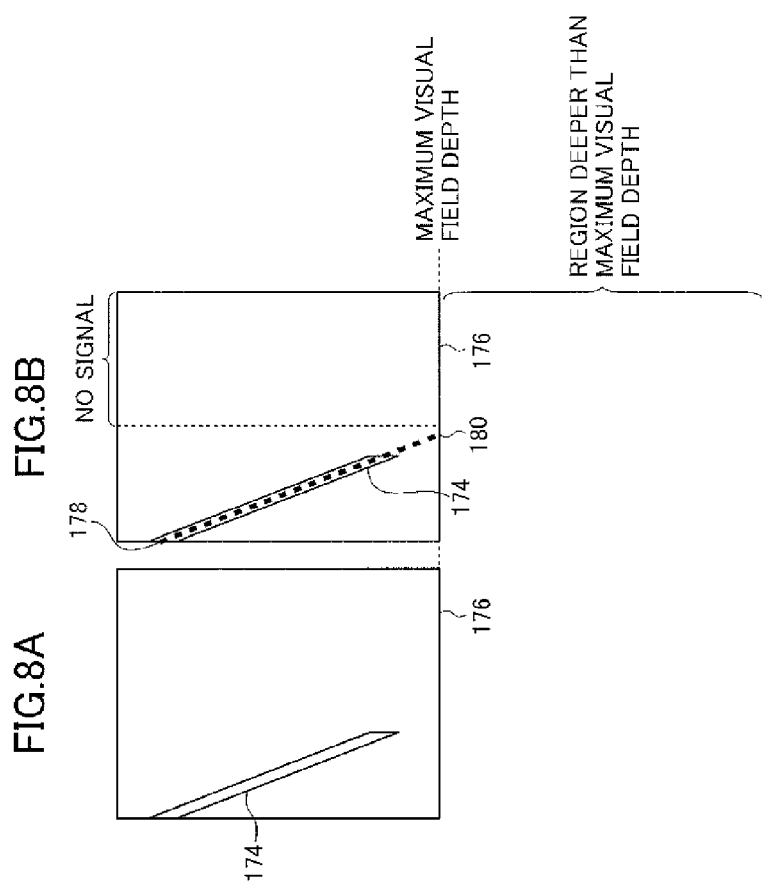

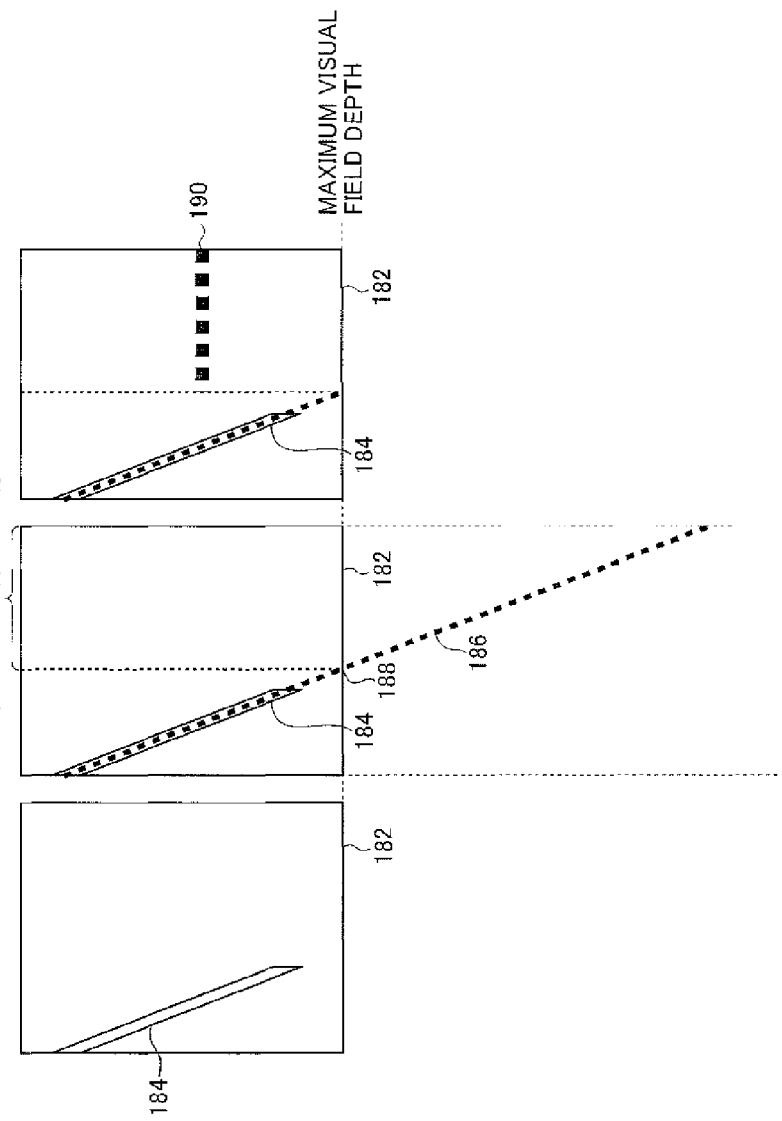

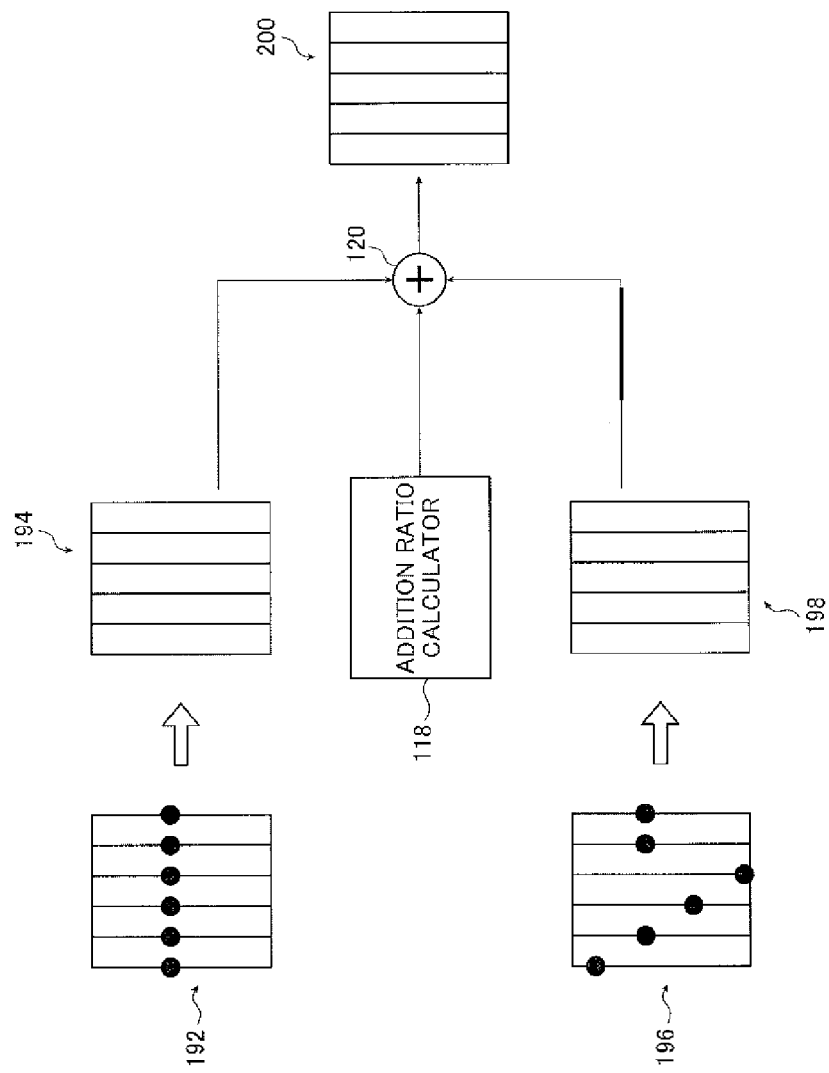

ULTRASOUND IMAGE GENERATING APPARATUS

BACKGROUND OF THE INVENTION

The present invention relates to an ultrasound image generating apparatus and particularly to an ultrasound image generating apparatus for displaying a puncture device together with a body tissue on a monitor screen.

In medical fields, ultrasound image generating apparatuses are widely used for diagnoses and examinations. An ultrasound image generating apparatus is used with an ultrasound probe. The ultrasound probe emits ultrasonic waves to a subject, whereupon the ultrasound image generating apparatus generates an ultrasonic tomographic image of the subject from an echo signal generated as the ultrasonic waves are reflected by the subject (hereinafter referred to as ultrasound image).

The ultrasound probe comprises a piezoelectric device array composed of a plurality of arrayed piezoelectric devices; the ultrasound probe emits ultrasonic waves from the piezoelectric device array to the subject and receives an echo signal from the subject. The ultrasound image generating apparatus generates an ultrasound image of the subject based on the echo signal received by the ultrasound probe and displays the generated image on the monitor.

In order to view a particular imaging target with a high definition, ultrasound image generating apparatuses use electronic focusing to align the focal point position with an imaging target position.

Electronic focusing means actuating a plurality of piezoelectric devices with a temporal difference so that the ultrasonic waves emitted from the piezoelectric devices align with each other in phase at the focal point position and likewise performing delay addition such that the echo signals received from the focal point position by the piezoelectric devices are temporally in phase. Near the focal point position, high-resolution tomographic image information can be obtained.

With ultrasound image generating apparatuses, paracentesis is performed by inserting a puncture needle into a desired site to obtain a tissue sample for definitive diagnosis. JP 2008-188178 A describe an apparatus wherein, in performing a paracentesis, a puncture guideline for performing a paracentesis is displayed on a monitor to permit changing the focal point position of electronic focusing in the array direction of the piezoelectric device array in order to acquire high-resolution tomographic image information at a target position in the focal point depth direction.

SUMMARY OF THE INVENTION

However, the apparatus described in JP 2008-188178 A can only obtain a good image quality of a site in focus but cannot obtain a good image quality of a site out of focus. In particular, where a doctor checks an ultrasound image while inserting a puncture needle, it is essential that the focus is placed on the puncture needle so that the puncture needle can be clearly observed, but unless other sites out of focus are also clearly observable, visibility of peripheral tissues decreases, and puncture efficiency are also reduced.

The present invention has been made in view of the above and has an object to provide an ultrasound image generating apparatus capable of preventing deterioration of image quality in the whole ultrasound image and generating an ultrasound image having a good image quality even near an imaging target such as the puncture needle.

To achieve the above objects, the ultrasound image generating apparatus of the invention comprises probe control means for causing a probe to transmit and receive waves; focal point control means for controlling a focal point of ultrasonic waves transmitted and received by the probe for each of transmission sound rays; the probe control means causing the probe to transmit a first ultrasonic waves having a focal point located by the focal point control means at an imaging target position and second ultrasonic waves having a focal point located by the focal point control means at a uniform position; weighted addition means for performing weighted addition of a first echo signal received upon transmission of the first ultrasonic waves and a second echo signal received upon transmission of the second ultrasonic waves to obtain a synthesized echo signal; and image generating means for generating an ultrasound image from the synthesized echo signal obtained by the weighted addition means.

Further, the weighted addition means determines weights to be used in the weighted addition for each of reception sound rays in the first echo signal and the second echo signal based on both the depth of the focal point for each of the transmission sound rays in the first ultrasonic waves and the depth of the focal point for each of the transmission sound rays in the second ultrasonic waves.

Further, weighted addition means changes the weights used in the weighted addition according to the increase in depth of the reception sound rays in the first echo signal and the second echo signal to undergo the weighted addition.

The present invention, enables enhancing the imaging target such as the puncture needle, preventing deterioration of image quality in the whole ultrasound image, and generating an ultrasound image having a good image quality even in a region other than the imaging target.

BRIEF DESCRIPTION OF THE DRAWINGS

FIG. 5 is a flow chart for determining a focal point position of ultrasonic waves for acquiring a first echo signal.

FIGS. 6A to 6G are schematic views illustrating an outline of weighted addition of the first echo signal and a second echo signal.

FIGS. 7A to 7D are graphs illustrating weighting of the first echo signal and the second echo signal.

FIG. 8A is a view illustrating an example where a puncture needle is inserted at an angle close to perpendicularity. FIG. 8B is a view illustrating a range where the first echo signal is to be acquired.

FIG. 9A is a view illustrating an example where a puncture needle is inserted at an angle close to perpendicularity. FIG. 9B is a view where the focus is placed on a puncture needle and the extension of the puncture needle. FIG. 9C is a view where the focal point position where the first echo signal is to be acquired is partially changed.

FIG. 10 is a view illustrating another example of the image processing performed in the ultrasound image generating apparatus according to the embodiment 1.

DETAILED DESCRIPTION OF THE INVENTION

Embodiments of the present invention will be described below based on the appended drawings.

Embodiment 1

Figure 1:
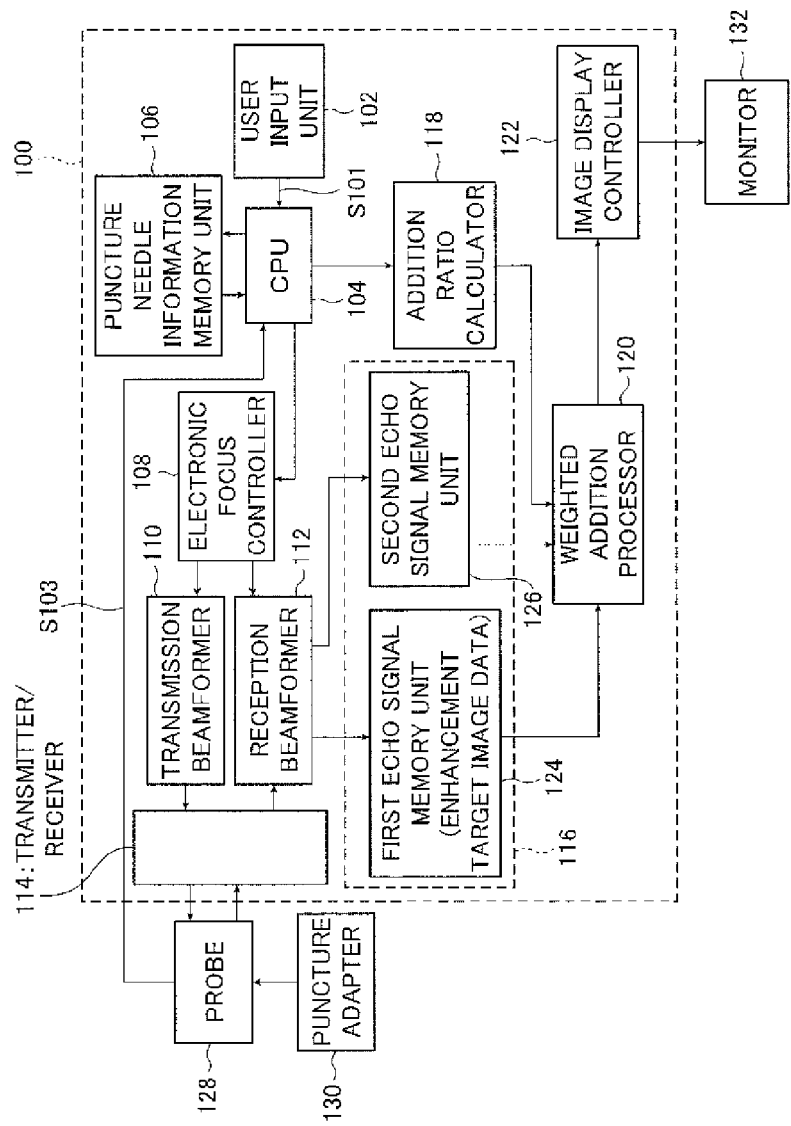
FIG. 1 is a function block diagram illustrating a configuration of the ultrasound image generating apparatus according to an embodiment 1.

FIG. 1 is a function block diagram illustrating a configuration of an ultrasound image generating apparatus 100 according to the embodiment 1 of the present invention.

The image generating apparatus 100 illustrated in that drawing comprises a user input unit 102, a CPU 104, a puncture needle information memory unit 106, an electronic focus controller 108, a transmission beamformer 110, a reception beamformer 112, a transmitter/receiver 114, an image memory unit 116, an addition ratio calculator 118, a weighted addition processor 120, and an image display controller 122. The image memory unit 116 comprises a first echo signal memory unit 124 and a second echo signal memory unit 126.

FIG. 1 also shows a probe 128, a puncture adapter 130, and a monitor 132 used with the ultrasound image generating apparatus 100. The probe 128 comprises a piezoelectric device array including a plurality of piezoelectric devices (see FIG. 2) and transmits and receives ultrasonic waves. The puncture adapter 130 is connected to the probe 128 and serves as a guide for inserting the puncture needle into a subject at a given angle. Specifically, the puncture needle moves in a given direction as it moves along the hole provided in the puncture adapter. The puncture adapter 130 is detachable from the probe 128, and the diameter of a usable puncture needle depends on the kind of puncture adapter 130. The angle at which the puncture needle is inserted into the subject (hereinafter referred to as insertion angle) or the position in which the puncture needle is inserted into the subject (hereinafter referred to as insertion position) also depend on the kind of puncture adapter 130. When the insertion angle and the insertion position are determined, the path along which the puncture needle is inserted into the subject (hereinafter referred to as insertion path) is determined. Accordingly, the diameter of a usable puncture needle, the insertion angle, the insertion position, and the insertion path thereof can be changed by exchanging the puncture adapter 130. The puncture adapter 130 comprises a memory unit in which the diameters of puncture needles that may be used by the puncture adapter and insertion angle information are previously stored. The puncture adapter 130, when connected to the probe 128, outputs the diameter of the puncture needle, the insertion angle, or the insertion position to the probe 128.

The user input unit 102 is provided to receive input from a user and receives the input of information on the puncture needle such as, for example, the diameter of the puncture needle and the insertion angle and outputs the information (S101) to the CPU 104. The user input unit 102 is, for example, an input switch or a keyboard.

The CPU 104 controls the operation in the ultrasound image generating apparatus 100 and writes into memory units among other functions. Upon receiving the information (S101) on the puncture needle outputted from the user input unit 102, the CPU 104 stores the information on the puncture needle in the puncture needle memory unit 106. Further, the CPU 104 stores information (S103) on the puncture needle outputted from the puncture adapter 130 via the probe 128 in the puncture needle memory unit 106. The information on the puncture needle specifically includes the diameter of the puncture needle, the insertion angle, the insertion position, or the insertion path.

The ultrasound image generating apparatus 100 uses information on the puncture needle to generate a synthesized echo signal from an echo signal acquired by focusing ultrasonic waves on the puncture needle and the extension of the puncture needle and an echo signal acquired by focusing ultrasonic waves on a uniform position. The uniform position herein means a position that is not dispersed over the whole area. Examples thereof include a case where the focal point positions are aligned with a fixed depth, a case where the focal point position gradually decreases from left to right in an image, and a case where the depth of the focal point position is reduced locally. Hereinafter, an echo signal acquired by focusing on an imaging target is referred to as first echo signal (target enhanced image data) and an echo signal acquired by focusing on a uniform position is referred to as second echo signal. A B-mode image generated by conversion of the first echo signal through processing such as interpolation into an image signal is referred to as first image (target enhanced image); a B-mode image generated by conversion of the second echo signal into an image signal is referred to as second image. Explanation of this embodiment will be made by describing a case where the focal point positions of ultrasonic waves are placed on the puncture needle and the extension of the puncture needle with the puncture needle as imaging target in the first image and the focal point positions of ultrasonic waves are aligned with a fixed depth in the second image as a representative example. In this embodiment, the image sizes of the first image and the second image are the same.

The CPU 104 determines the focal point position in accordance with the insertion path of the puncture needle based on information on the puncture needle stored in the puncture needle memory unit 106 and outputs a signal designating the focal point position to an electronic focus controller 108. The CPU 104 further outputs a predetermined uniform focal point position to the electronic focus controller 108. For a visual field depth of 50 mm as for a breast, for example, the focal point position is fixedly set to a depth of 20 mm. The visual field depth means the depth from a surface of the subject and a depth at which an echo signal is acquired.

The electronic focus controller 108 controls the electronic focusing. The electronic focus controller 108 calculates the actuation timing of the individual piezoelectric devices in the probe 128 based on the focal point position determined by the CPU 104 and outputs the actuation timing to the transmission beamformer 110. Further, the electronic focus controller 108 outputs a delay amount in echo signal delay addition according to the depth at which the echo signal is generated to the reception beamformer 112.

The transmission beamformer 110 operates a pulser provided in the transmitter/receiver 114 to form a transmission beam designated by the electronic focus controller 108 in the probe 128. Specifically, the transmission beamformer 110 outputs an instruction for operating the pulser provided in the transmitter/receiver 114 to the transmitter/receiver 114 according to the actuation timing of the individual piezoelectric devices outputted from the electronic focus controller 108.

The transmitter/receiver 114 performs signal transmission and reception with the probe 128. The transmitter/receiver 114 comprises a pulser, an amplifier, a low pass filter, and an A/D converter for generating a high-voltage electric signal for actuating the piezoelectric devices in the probe 128. The transmitter/receiver 114 operates the pulser according to an instruction outputted from the transmission beamformer 110 and outputs an electric signal for actuating the piezoelectric devices (hereinafter referred to as piezoelectric device actuating signal) to the probe 128. Further, the transmitter/receiver 114 amplifies the signal outputted from the probe 128, cuts out the radio frequency component through the low pass filter, and, after A/D conversion, outputs the signal to the reception beamformer 112.

The probe 128 transmits and receives ultrasonic waves to the subject and is used in contact with the subject, which may be, for example, a patient. The probe 128 comprises a piezoelectric device array including a plurality of piezoelectric devices and an analog multiplexer and transmits and receives ultrasonic waves with the plurality of piezoelectric devices. The probe 128 switches between the piezoelectric devices to be actuated in sequence according to an electric signal outputted from the transmitter/receiver 114 to perform electronic scan. The probe 128 receives an echo signal representing ultrasonic waves reflected by the subject with piezoelectric devices, converts the signal into an electric signal, and outputs the signal to the transmitter/receiver 114.

The reception beamformer 112 delays the echo signals outputted from the transmitter/receiver 114 according to the delay amounts outputted from the focus controller 108 and the positions at which the echo signals were generated in order to align their phases and add these echo signals to generate reception sound rays (hereinafter, the phase-aligned, added echo signals will be referred to as reception sound rays). The reception beamformer 112 stores the first echo signal of which the reception sound ray has been generated in the echo signal memory unit 124 and the second echo signal of which the reception sound ray has been generated in the second echo signal memory unit 126.

The addition ratio calculator 118 calculates the addition ratio of the first echo signal and the second echo signal. The addition ratio calculator 118 calculates the addition ratio with which the first echo signal and the second echo signal are added based on the focal point position outputted from the CPU 104 and outputs the calculated ratio to the weighted addition processor 120. Thus, a synthesized image is obtained by adding the first echo signal and the second echo signal with a desirable ratio.

The weighted addition processor 120 performs weighted addition of the first echo signal stored in the first echo signal memory unit 124 and the second echo signal stored in the second echo signal memory unit 126 according to the addition ratio outputted from the addition ratio calculator 118 and outputs the result to the image display controller 122.

The image display controller 122 generates an image signal, which is tomographic image information pertaining to a tissue in the subject, from the echo signal (reception sound ray). The image display controller 122 comprises an STC (sensitivity time control) and a DSC (digital scan converter). The STC corrects attenuation due to distance in accordance with the depth of the reflection location of the ultrasonic waves for the synthesized echo signal generated by the weighted addition processor 120. The DSC converts the image data corrected by the STC into a type in accordance with an ordinary television signal scanning method (raster conversion) and performs required image processing such as contrast processing to generate an image signal. The monitor 132 displays an ultrasound image according to the image signal generated by the image display controller 122.

Figure 2:
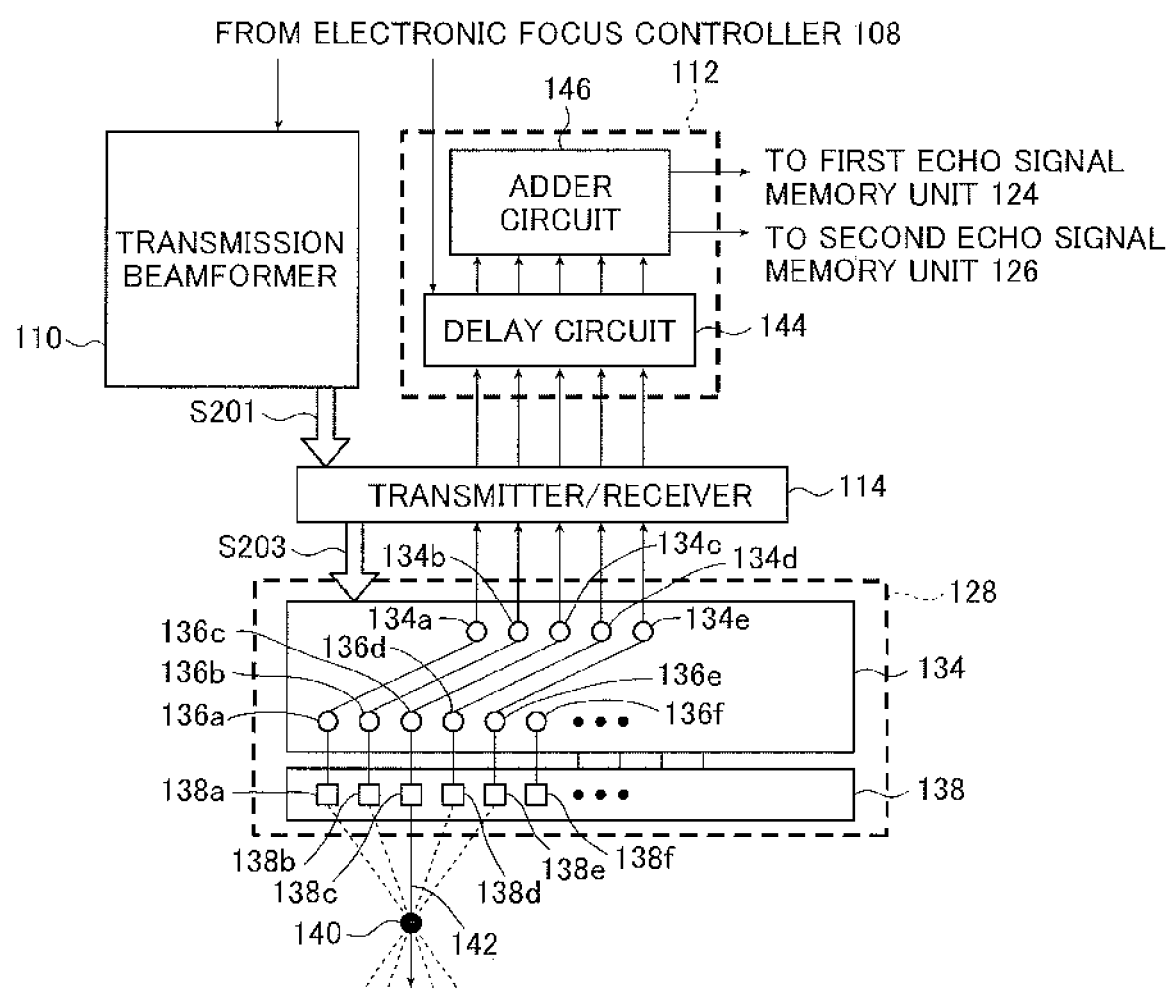
FIG. 2 is a schematic view illustrating a detailed configuration of a probe and a reception beamformer according to the embodiment 1.

FIG. 2 is a schematic view illustrating a detailed configuration of the probe 128 and the reception beamformer 112. The probe 128 comprises an analog multiplexer 134 and a piezoelectric device array 138. In the drawing, the puncture adapter 130 and the signal outputted from the puncture adapter 130 are omitted.

The piezoelectric device array 138 comprises a plurality of piezoelectric devices (in FIG. 2, only six of them, 138a to 138f, are shown) arranged unidimensionally. The piezoelectric devices (e.g., 138a to 138f) are connected to the corresponding output terminals (e.g., 136a to 134f) of the analog multiplexer 134.

The analog multiplexer 134 is an analog electronic switch and comprises five channels of input/output terminals (134a to 134e in FIG. 2) for exchanging signals with the transmitter/receiver 114 and a plurality of input/output terminals connected one-to-one with the respective piezoelectric devices in the piezoelectric device array 138 for exchanging signals. A description will now be made of the six input/output terminals indicated as input/output terminals 136a to 136f. The analog multiplexer 134 selects a piezoelectric device to be actuated by switching between the connections between the five-channel input/output terminals 134a to 134e connected to the transmitter/receiver 114 and the input/output terminals 136a to 136f connected to the piezoelectric device array 138. For example, connecting the input/output terminal 134a to the input/output terminal 136a enables the piezoelectric device 138a to be actuated. In this embodiment, ultrasonic waves are transmitted and received by means of five piezoelectric devices connected via the analog multiplexer 134.

Upon receiving an instruction (S201) from the transmission beamformer 110, the transmitter/receiver 114 outputs a piezoelectric device instruction signal (S203) to the analog multiplexer 134. While the transmitter/receiver 114 actually outputs five kinds of signals corresponding to the five-channel input/output terminals of the analog multiplexer 134, the drawing only shows one arrow for the sake of clarity.

The analog multiplexer 134 uses the piezoelectric device instruction signal (S203) outputted from the transmitter/receiver 114 to connect the five-channel input/output terminals 134a to 134e connected to the transmitter/receiver 114 and the input/output terminals 136a to 134f connected to the piezoelectric device array 138. By way of example, the drawing shows connections between the input/output terminals 134a and 136a, 134b and 136b, . . . , 134e and 136e, respectively. As will be seen, elements given an identical alphabetical character as the input/output terminal 134a, the input/output terminal 136a, and the piezoelectric device 138a are formed into one line and connected.

The transmitter/receiver 114 outputs a piezoelectric device actuating signal (S203) having a different actuation timing for each piezoelectric device from the inner pulser according to an instruction outputted from the transmission beamformer 110. The piezoelectric devices 138a to 138e emit ultrasonic waves at timings designated by the piezoelectric device actuating signal and transmit ultrasonic waves having a focal point coinciding with a predetermined position. That is, the ultrasonic waves outputted from the piezoelectric devices 138a to 138e come in phase with each other at a focal point position 140 designated by the CPU 104 and come into focus. Thus, the ultrasound image generating apparatus 100 emits ultrasonic waves focusing on a desired position from the probe 128. An arrow 142 in FIG. 2 indicates the center line of the sensitivity distribution of ultrasonic waves transmitted by the piezoelectric devices 138a to 138e, and the center line is called transmission sound ray.

The piezoelectric devices 138a to 138e receive and converts echo signals generated as emitted ultrasonic waves are reflected by the subject into electric signals and transmit these signals from the analog multiplexer 134 to the transmitter/ receiver 114. The transmitter/receiver 114 amplifies the echo signals, causes the echo signals to pass through the low pass filter, and, after A/D conversion, outputs the echo signals to a delay circuit 144 in the reception beamformer 112.

The piezoelectric devices 138a to 138e, located at different distances from the arrow 142, receive echo signals generated at individual points on the arrow 142 at different timings. The delay circuit 144 delays the echo signals so that the echo signals outputted from the piezoelectric devices 138a to 138e come temporally in phase with each other. In this example, because the piezoelectric device 138c is located closest to the arrow 142, the echo signal outputted by the piezoelectric device 138c is delayed most and the echo signals outputted by the piezoelectric devices 138b and 138d are also delayed so that the echo signals outputted by the piezoelectric devices 138a and 138e and the echo signals outputted by the other piezoelectric devices come temporally in phase with each other.

An adder circuit 146 adds echo signals placed in phase with each other and generates and outputs the reception sound ray to the image memory unit 116. Thus, the reception beamformer 112 delays and adds the echo signals received by the piezoelectric devices to generate the reception sound ray. The reception sound ray is converted into an image signal through interpolation and other processing to generate an ultrasound image.

The analog multiplexer 134 switches between the inner terminals to select a piezoelectric device to be used one after the other in the array direction to achieve electronic scan. More specifically, upon receiving the echo signal of the ultrasonic waves transmitted from the transmission sound ray 142, the analog multiplexer 134 connects the input/output terminal 134a to the input/output terminal 136b, the input/output terminal 134b to the input/output terminal 136c, . . . , the input/output terminal 134e to the input/output terminal 136f, so that the piezoelectric devices to be used next are 138b to 138f. The piezoelectric devices 138b to 138f emit ultrasonic waves at timings such that they come temporally in phase with each other at a focal point position designated by the CPU 104. This electronic scan shifts the transmission sound ray in position by a given distance in the piezoelectric device array direction. The ultrasound image generating apparatus 100 causes the probe 128 to effect the electronic scan to acquire a plurality of echo signals and converts the echo signals into image signals to produce a two-dimensional image.

The ultrasound image generating apparatus 100 transmits and receives ultrasonic waves by focusing on the puncture needle and on the extension of the puncture needle for each transmission sound ray in the first image and focusing on a predetermined uniform position in the second image.

Figure 3:
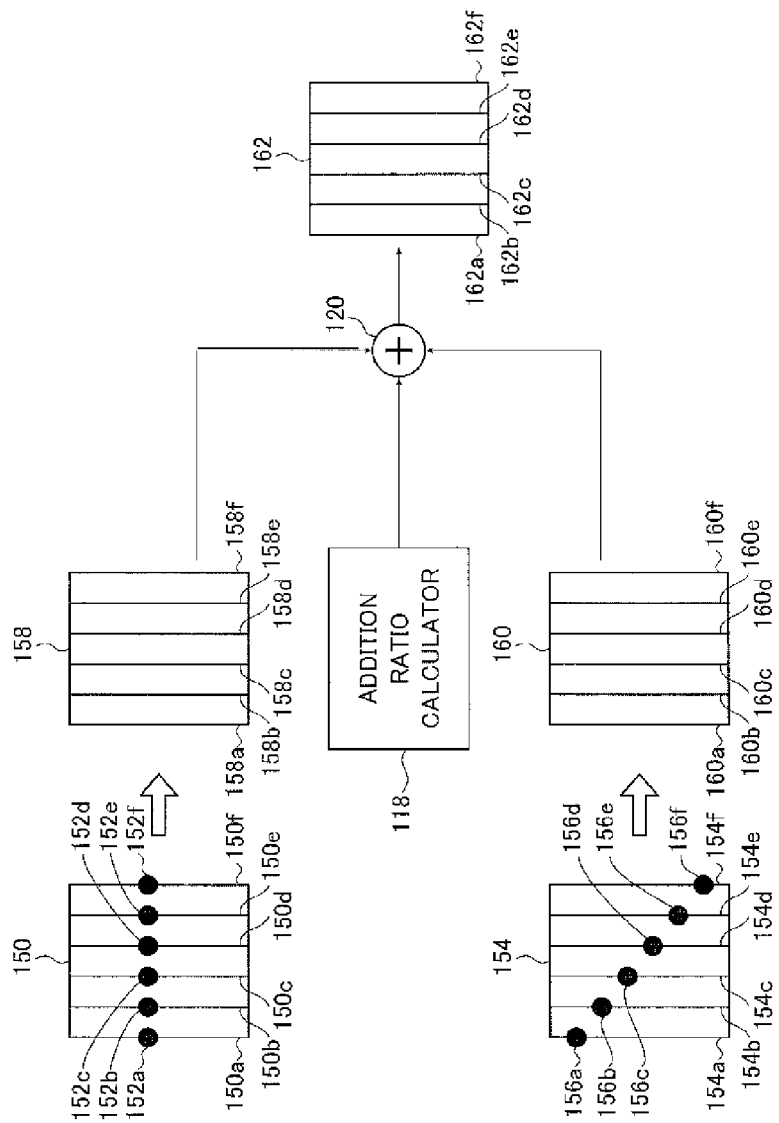
FIG. 3 is a schematic view illustrating an outline of image processing preformed in the ultrasound image generating apparatus according to the embodiment 1.

FIG. 3 is a schematic view illustrating an outline of the image processing performed in the ultrasound image generating apparatus 100 according to this embodiment. FIG. 3 specifically illustrates a flow in which a transmission beam 150 is used to acquire a second echo signal 158, which is an echo signal, and a transmission beam 154 is used to acquire a first echo signal 160, whereupon the second echo signal 158 and the first echo signal 160 are added to acquire a synthesized echo signal 162. In FIG. 3, the transmission beam 150 and the transmission beam 154 are illustrated so that the transmission sound rays of ultrasonic waves transmitted from the probe 128 are arranged in the scan direction of the probe 128, and an upper side and a lower side are added for ease of understanding (the same applies to the drawings illustrating transmission sound rays and reception sound rays below).

The transmission beam 150 comprises transmission sound rays 150a to 150f; the transmission beam 154 comprises transmission sound rays 154a to 154f. Black dots 152a to 152f and black dots 156a to 156f indicate focal point positions on the corresponding transmission sound rays 150a to 150f and transmission sound rays 154a to 154f. For example, the focal point on the transmission sound ray 150a is located at the focal point position 152a; the focal point on the transmission sound ray 150b is located at the focal point position 152b. In the transmission beam 150, the focal points 152a to 152f are located at the same depth. In the transmission beam 154, the focal points 156a to 156f are located on the puncture needle and the extension of the puncture needle. The upper side of the transmission beam 150 represents the position at which the probe 128 comes into contact with the subject such as a patient while the lower side of the transmission beam 150 represents a maximum value of the visual field depth (maximum visual field depth). The maximum visual field depth is a maximum depth for acquiring an ultrasound image. The maximum visual field depth is determined by a depth at which an echo signal is acquired and may be determined by the user.

The ultrasound image generating apparatus 100 uses the transmission beam 150 having focal point positions aligned with a fixed depth to acquire the second echo signal 158 and uses the transmission beam 154 having focal point positions placed on the puncture needle and the extension of the puncture needle to acquire the first echo signal 160. The second echo signal 158 comprises reception sound rays 158a to 158f; the first echo signal 160 comprises reception sound rays 160a to 160f. The reception sound rays 158a to 158f and the transmission sound rays 150a to 150f correspond to each other so that a depth on which focus is placed in the reception sound ray 158a is the depth of the focal point 152a. In other words, the best image quality in the reception sound ray 158a is obtained at a depth position corresponding to the focal point 152a. The relationship between the reception sound rays 160a to 160f and the transmission sound rays 154a to 154f is the same as the relationship between the transmission sound rays 158a to 158f and the reception sound rays 150a to 150f.

The second echo signal 158 thus obtained forms an image where focus is placed on the whole image at a fixed depth and not an image where a particular imaging target is enhanced. On the other hand, the first echo signal 160, which is focused on the puncture needle and the extension of the puncture needle, forms an image having a good image quality on the puncture needle and the extension of the puncture needle.

The ultrasound image generating apparatus 100 performs weighted addition of the second echo signal 158 (reception sound rays 158a to 158f) and the first echo signal 160 (reception sound rays 160a to 160f) for each of the reception sound rays to obtain the synthesized echo signal 162 (reception sound rays 162a to 162f). More specifically, the ultrasound image generating apparatus 100 performs weighted addition of the reception sound ray 158a and the reception sound ray 160a to obtain the reception sound ray 162a and performs weighted addition of the reception sound ray 158b and the reception sound ray 160b to obtain the reception sound ray 162b. Weighted addition is likewise performed of the other reception sound rays to generate the synthesized echo signal 162. Thus, the second echo signal 158 and the first echo signal 160 are added with appropriate weights to generate a desired synthesized echo signal. For the sake of clarity, the description has been made with six each of the transmission sound rays and the reception sound rays.

Figure 4:
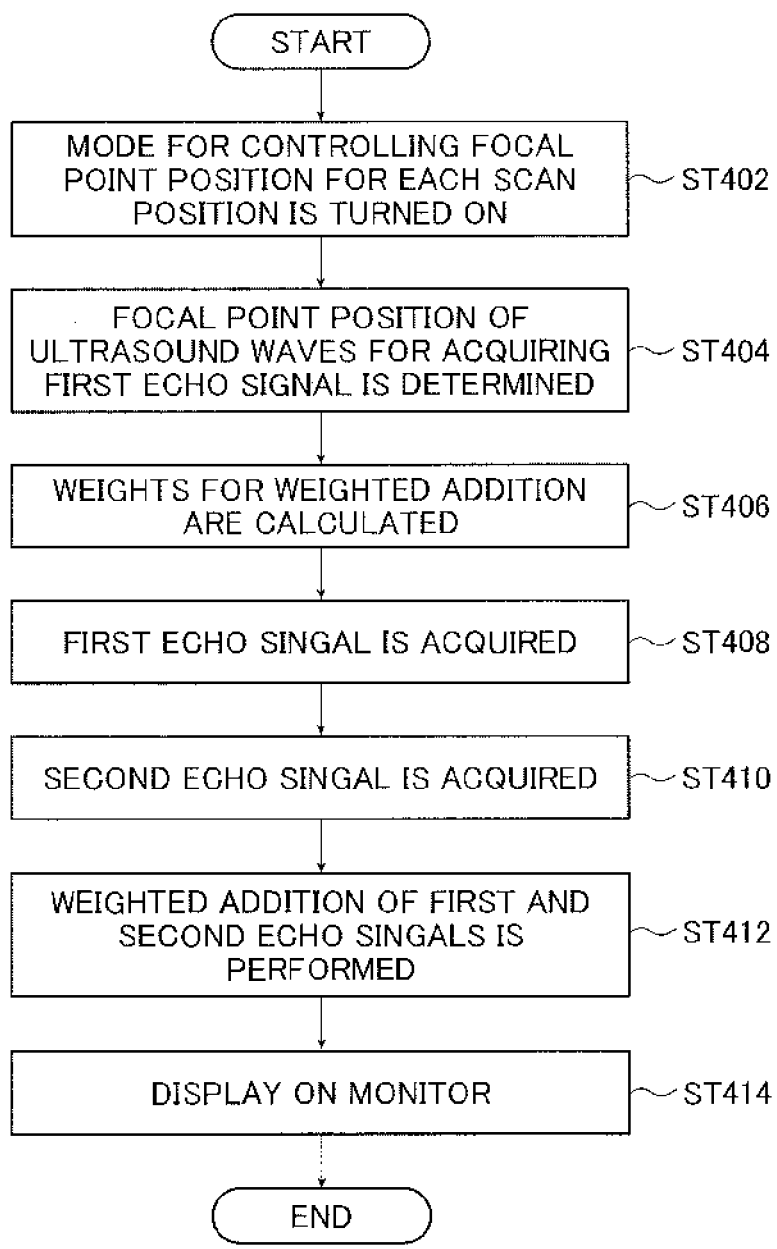
FIG. 4 is an operation flow chart of the ultrasound image generating apparatus according to the embodiment 1.

Referring now to the flowchart illustrated in FIG. 4, an outline of the operations and effects of the ultrasound image generating apparatus 100 will be described. First, the apparatus is switched on, and the focal point position control mode for controlling the focal point position for each scan position is turned on in the step ST402. The focal point position of ultrasonic waves for acquiring the first echo signal is determined in the step ST404, and the weight used for weighted addition is calculated in the step ST406. Ultrasonic waves are transmitted and received in the step ST408 at a focal point position determined in the step ST404 to acquire the first echo signal, and ultrasonic waves are transmitted and received at a predetermined fixed focal point position in the step ST410 to acquire the second echo signal. Weighted addition of the first echo signal and the second echo signal is performed in the step ST412, and a synthesized echo signal obtained is converted in the step S414 into an image signal, which is displayed on the monitor 132. The second echo signal and the first echo signal are acquired at different timings.

Referring now to the flowchart illustrated in FIG. 5, the operation in the step ST404 for determining the focal point position of ultrasonic waves for acquiring the first echo signal will be described in detail.

The ultrasound image generating apparatus 100 produces a table for focusing on the puncture needle from the diameter of the puncture needle, the insertion angle, the insertion position, or the insertion path stored in the puncture needle information memory unit 106 and stores the table in the puncture needle information memory unit 106 (the table for focusing on the puncture needle will be referred to as control line table below). The ultrasound image generating apparatus 100 determines the focal point position of ultrasonic waves for acquiring the first echo signal based on the control line table stored in the puncture needle information memory unit 106. Thus, the ultrasound image generating apparatus 100 focuses on the puncture needle and the extension of the puncture needle.

The focal point position control mode is turned on for each scan position in the step ST402, whereupon the control line table is read out in the step ST500. The user is inquired as to whether a read-out control line table is to be corrected in the step ST502. When the read-out control line table is not to be corrected, the procedure proceeds to the step ST504, where the control line table is made to be the focal point position of ultrasonic waves for acquiring the first echo signal, then proceeding to the step ST 406.

When the control line table is corrected in the step ST 502, puncture needle characteristics are extracted in the step ST506, and fitting of the control line table and the puncture needle is performed in the step ST508. The control line table is corrected to be the focal point position of ultrasonic waves for acquiring the first echo signal in the step ST510, proceeding to the step ST406. In the step ST406, weights for weighted addition are calculated. The ultrasound image generating apparatus 100 acquires the first echo signal by focusing on the position indicated by the corrected control line table. Such correction of the control line table enables acquisition of the first echo signal focused on the puncture needle even when the puncture needle is off the insertion path determined by the puncture adapter. The puncture needle deviates from the insertion path because of a play of the adapter itself, a deflection of the puncture needle due to a resistance of the tissue among other causes. The extraction of the puncture needle characteristics performed in the step ST506 may be achieved by obtaining the frame difference between different images to specify the puncture needle position.

Now, calculation of the addition ratio used for the weighted addition in the step ST406 will be described referring to FIGS. 6A to 6G. The reception sound ray L of a synthesized echo signal 170 obtained by performing the weighted addition of the first echo signal 164 and the second echo signal 166 is represented by a formula $L=(1-p) \times a + p \times b$. In the formula, a is the reception sound ray of the first echo signal 164, b is the reception sound ray of the second echo signal 166, and p is the weight of the second echo signal.

A basic idea for determining the addition ratio is that the position on which the second echo signal is focused is given a weight of 1 and the position on which the first echo signal is focused is given a weight of 0. In other words, for the position on which the second echo signal is focused, the second echo signal is the synthesized echo signal; for the position on which the first echo signal is focused, the first echo signal is the synthesized echo signal. Such control ensures that the image of a position in focus has a good image quality because it is used for the synthesized image.

By way of example, we will describe a case of weighted addition of the first echo signal 164 and the second echo signal 166 each composed of four reception sound rays and having an identical maximum visual field depth. When a leftmost reception sound ray 170a of the synthesized echo signal 170 illustrated in FIG. 6G is calculated, for example, the weighted addition of a leftmost reception sound ray 164a of the first echo signal 164 illustrated in FIG. 6E and a leftmost reception sound ray 166a of the second echo signal 166 illustrated in FIG. 6F is performed. Specifically, the reception sound ray 164a and the reception sound ray 166a are added with a weight indicated by a graph 168a in FIG. 6A. In the reception sound ray 170a, for example, as illustrated in FIG. 6A, the data of the reception sound ray 164a is the data of the reception sound ray 170a in a region from the depth 0 to the depth of a focal point 163a (a first region) because the weight 168a is 0 in that region, while the data of the reception sound ray 166a is the data of the reception sound ray 170a in a region where the depth is greater than the depth of a focal point 165a (a third region), because the weight 168a is 1 in that region.

Figure 6A:
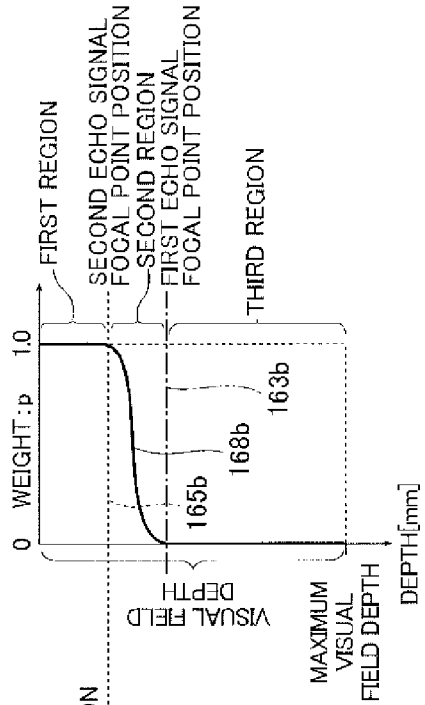

As illustrated in FIG. 6A, in a region where the depth is in a range from the depth of the focal point 163a to the depth of the focal point 165a (a second region), the weight 168a changes smoothly from 0 to 1, and the reception sound ray 164a and the reception sound ray 166a are added with that weight according to the above formula representing L, the result of the addition being the data of the reception sound ray 170a. In other words, in the region from the depth of the focal point 163a to the depth of the focal point 165a, the weight of the second echo signal 166 is increased as the depth increases. This is because the image quality of the second echo signal improves as the depth approaches the depth of the focal point 165a of the second echo signal from the depth of the focal point 163a of the first echo signal. In other words, the difference in image quality between the first echo signal 164 and the second echo signal 166 is incorporated into the weight, so that the weight of image data is increased as the image data is closer to the focal point position and, hence, has a better image quality. Changing the weight in the weighted addition according to the depth enables a smooth connection of the data on the reception sound ray 170a in the region from the depth of the focal point 163a to the depth of the focal point 165a. That is, the synthesized image has a good image quality because the difference in image quality between the first echo signal 164 and the second echo signal 166 for each visual field depth is considered in such a manner that the echo signal having the better image quality is given an increased weight in the weighted addition in producing the synthesized echo signal 170.

Figure 6B:
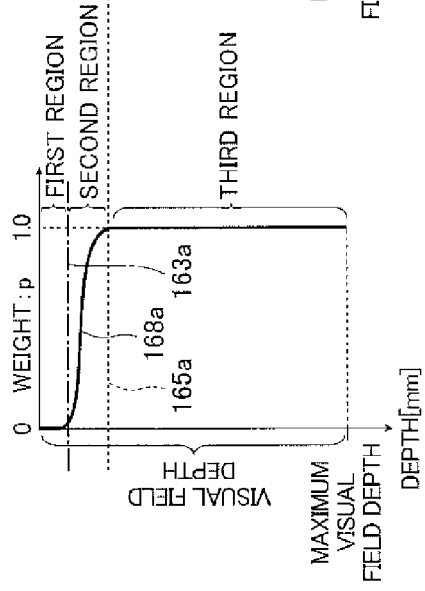
Figure 6E:
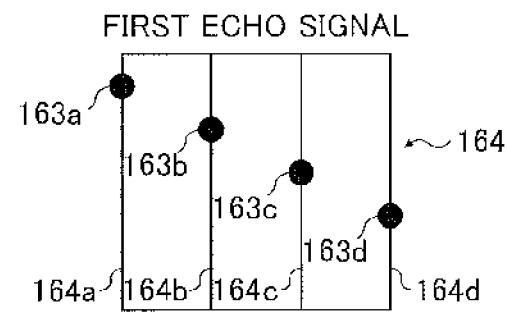
Figure 6F:
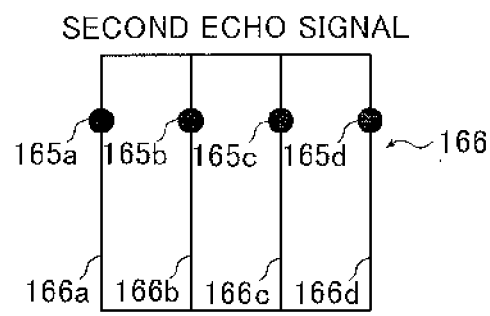
Figure 6G:
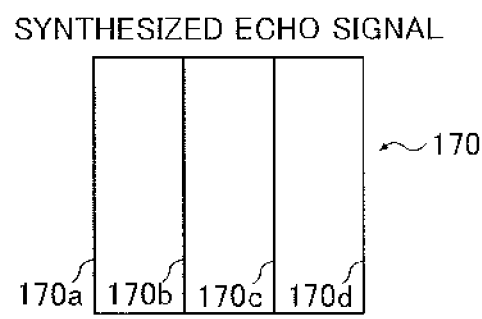

Likewise, to calculate the reception sound ray 170b, the reception sound ray 164b of the first echo signal 164 and the reception sound ray 166b of the second echo signal 166 are added with a weight 168b shown in FIG. 6B. Specifically, as illustrated in FIG. 6B, in the reception sound ray 170b, the data of the reception sound ray 166b is the data of the reception sound ray 170b in a region from the position of the depth 0 to the depth of a focal point 165b (a first region) because the weight 168b is 1 in that region, while the data of the reception sound ray 164b is the data of the reception sound ray 170b in a region where the depth is greater than the depth of a focal point 163b (a third region), because the weight 168b is 0 in that region. In a region where the depth is in a range from the depth of the focal point 165b to the depth of the focal point 163b (the second region), the weight 168b changes in a smooth curve from 1 to 0, and the reception sound ray 164b and the reception sound ray 166b are added with that weight according to the above formula representing L, the result of the addition being the data of the reception sound ray 170b. In other words, in the region from the depth of the focal point 165b to the depth of the focal point 163b, the weight of the second echo signal 164 is increased as the depth increases. This is because the image quality of the first echo signal 164 improves as the depth approaches the depth of the focal point 163b of the first echo signal 164. Data of a reception sound ray 170c and a reception sound ray 170d are obtained likewise as in the case of the reception sound ray 170b by performing the weighted addition of reception sound rays 164c and 166c with a weight 168c illustrated in FIG. 6C and the weighted addition of reception sound rays 164d and 166d with a weight 168d illustrated in FIG. 6D, respectively. The weighted addition performed as the weight is thus changed enables generation of an image focused on the puncture needle and the extension of the puncture needle while maintaining the quality of the whole image, which are the imaging targets. In the third region, a good image quality is obtained because only the image having the closer focal point position is used.

While FIGS. 6A to 6G illustrate a case of four reception sound rays for ease of explanation, actual apparatuses use more than four reception sound rays. In cases using more than four reception sound rays, weighting graphs smoothly connecting the focal point positions of the first echo signal and the second echo signal are required in a number equal to the number of the reception sound rays. When the reception sound rays of the first echo signal and the second echo signal having a focal point located at the same depth are added, addition may be performed, for example, with a weight of 0.5 for each image, or only one of the reception sound rays may be used.

FIGS. 7A to 7D illustrate examples of other weighting graphs for weighted addition of the first echo signal 164 and the second echo signal 166. The graphs illustrated in FIGS. 7A to 7D are the same as FIGS. 6A to 6D, respectively in that in a region (the first region) shallower than the shallower focal point position, the image data having the shallower focal point position is given a weight of 1 and that the weight is changed smoothly between the focal point position of the first echo signal 164 and the focal point position of the second echo signal 166 (second region), but are different in the change of the weight in a region deeper than the second region (third region). Specifically, while in the case shown in FIGS. 6A to 6G, weighting is such that in a region deeper than the deeper focal point position, one of the second echo signal and the first echo signal is given a weight of 1, the weighting in the graphs shown in FIG. 7A to 7D is not such that one of the echo signals is given a weight of 1 but the weighted addition is performed with a weight in accordance with the depth.

In a graph 172a in FIG. 7A showing the addition ratio of the reception sound ray 164a and the reception sound ray 166a, the weight gradually decreases from 1 and settles at 0.5 in the third region. More specifically, at a depth of the focal point 165a, the data of the reception sound ray 165a of the second echo signal 166 is the data of the reception sound ray 170a of the synthesized echo signal 170, and in the third region, the weight of the second echo signal 166 decreases as the depth increases until the weight of the individual image data settles at 0.5. Thus, in a region deeper than the depth of the focal point 165a, the images can be smoothly connected as the effects of speckle noise are reduced.

Figures 7C, 7D:
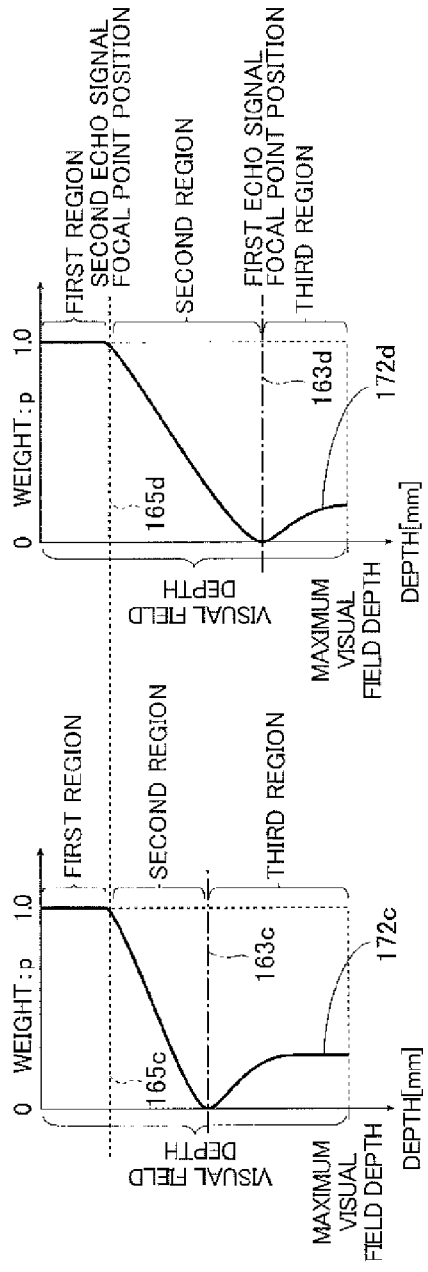

In a graph 172b in FIG. 7B showing the addition ratio of the reception sound ray 164b and the reception sound ray 166b, the weight smoothly increases from 0 as the depth increases and saturates without reaching 0.5 in the third region. That is, at a depth deeper than the depth of the focal point 163b, the weight of the second echo signal 166 gradually increases while the weight of the first echo signal 164 gradually decreases, but addition is made with the first echo signal 164 given the greater weight than the second echo signal 166 even at a position where the depth reaches a maximum. This is due to the fact that the first image has the better image quality than the first image in a region deeper than the depth of the focal point position 163b because the focal point position of the first echo signal is at a greater depth than the focal point position of the second echo signal. Likewise, in a graph 172c shown in FIG. 7C, the weight of the second echo signal 166 becomes 0 at a depth of the focal point 163c and gradually increases as the depth increases from the depth of the focal point 163c. At a position corresponding to the maximum depth, the weight of the second echo signal 166 is smaller than in the graph 172b. This is due to the fact that because the focal point depth of the first echo signal is at a deeper position, the image quality of the synthesized echo signal 170 is improved more when the first echo signal 164 is given a greater weight. Likewise, in a graph 172d shown in FIG. 7D, the weight of the second echo signal 166 is smaller than in the graph 172c at a position where the depth reaches the maximum. Determining the weights of the individual images as described above enables a smooth connection of images while reducing the speckle noise and thus improves the image quality after the addition is made.

As described above, according to the embodiment 1 of the ultrasound image generating apparatus 100 of the invention, the first echo signal acquired with the focal points placed on the puncture needle and the second echo signal acquired with the focal points aligned with a fixed depth are obtained, and the weights for addition of the first echo signal and the second echo signal are determined according to the focal point positions of the respective echo signals, i.e., the image qualities. Further, because the ultrasound image generating apparatus 100 performs weighted addition of the first echo signal and the second echo signal using weights determined according to the focal point positions to obtain the synthesized echo signal, the ultrasound image generating apparatus 100 is capable of generating an ultrasound image having a good image quality even in an area around an imaging target while preventing reduction in quality of the whole ultrasound image.

Another mode of processing in a case where the focus is placed on the puncture needle will be described referring to FIGS. 8A and 8B. A case where, as illustrated in FIG. 8A, a puncture needle 174 is inserted at an angle close to perpendicularity in an image display region 176 will be considered. In this case, because the extension of the puncture needle 174 intersects the lower side of the image display region 176 as illustrated in FIG. 8B, if a focal point 178 is placed on the puncture needle 174, the focus is placed outside of the image display region 176 starting with a certain point. Should any of the weighting graphs described in FIGS. 6A to 6G or FIGS. 7A to 7D be used in such case, weighted addition is performed enhancing data focused on a position exceeding the maximum visual field depth, resulting in a reduced image quality within the image display region 176. Therefore, in the region on the right side of a point 180 in the drawing where the extension of the puncture needle 174 intersects the lower side of the image display region 176, control is so made that the ultrasonic waves for acquiring the first echo signal are not transmitted or the first echo signal is not acquired in order not to perform weighted addition itself related to the first echo signal. For a region where the focal point depth exceeds the image display region 176, the weight of the first echo signal may be set to 0 and the weight of the second echo signal may be set to 1. Such control also enables acquisition of an image focused on the puncture needle 174 and generation of an image of which the image quality does not decrease even in a region having a focal point position outside of the image display region 176.

In this case, whether the extension of the puncture needle 174 as shown intersects the lower side of the image display region 176 is determined through calculation by the CPU 104 from the insertion position of the puncture needle 174, its insertion angle, and the size of the image display region 176.

Another mode of processing in a case where the focus is placed on the puncture needle will be described referring to FIGS. 9A to 9B. Also in FIG. 9A as in FIG. 8A, a case where a puncture needle 184 is inserted at an angle close to perpendicularity in an image display region 182 will be considered. Also in this case, because the puncture needle 184 and a broken line 186 representing focal point positions lying on the extension of the puncture needle 184 intersects the lower side 188 of an image display region 182, if the focus is placed on the puncture needle 184 and the extension of the puncture needle 184, the focal point position is located on the outside of the image display region 182, i.e., at a position deeper than the maximum visual field depth in the region on the right side of a point 188 in the drawing. Here, control is so made that the focal point position located in a region outside of the image display region 182 is replaced by any depth 190 within the image display region 182. Said any depth to replace such focal point may be at the same depth as the focal point in the second echo signal or may be determined by the user. Such control ensures that the focal point position is not located outside of the image display region 182 and the image quality is not reduced.

FIG. 10 illustrates an outline of the weighted addition processing performed when the focal point position is controlled as described above. Also in this case, weighted addition is performed of a second echo signal 194 acquired by using a transmission beam 192 having the focal point depths aligned with a fixed depth and a first echo signal 198 acquired by using a transmission beam 196 having the focal point depths located at the puncture needle or at the extension of the puncture needle and having the focal point depths aligned with a fixed depth for a region where the puncture needle or the extension of the puncture needle is outside of the image display region in order to obtain a synthesized echo signal 200. The weights for weighted addition of the second echo signal 194 and the first echo signal 198 may be those represented by the same graphs as illustrated in FIGS. 6A to 6D or FIGS. 7A to 7D.

Although this embodiment has been described by way of an example where the puncture adapter is used, the puncture adapter need not necessarily be used. Because the puncture position varies due to individual differences among subjects, puncture may be a freehand puncture. In such case, the user enters the diameter, the insertion angle, the insertion position, or the insertion path of the puncture needle by means of the user input unit. Alternatively, the puncture needle is inserted to obtain the frame difference, puncture needle characteristics are extracted, and straight lines and curves are subjected to fitting according to the extracted characteristics to calculate the insertion angle, the insertion position, or the insertion path of the puncture needle and produce a fresh control line table. The newly produced table may be stored for a next use. Thus, the focus may be achieved on the puncture needle using the characteristics of the puncture needle in a differential image as information on the puncture needle.

Note that also when the puncture adapter is used, such information as the insertion angle, the insertion path, or the insertion position of the puncture needle need not necessarily be acquired from the puncture adapter. For example, as in the case of a freehand puncture, the control line table may be produced by obtaining the frame difference to extract puncture needle characteristics, and performing fittings of straight lines and curves according to the extracted characteristics or the user may enter the control line table. This obviates the necessity to acquire information on the puncture needle from the puncture adapter and hence simplifies the structure of the puncture adapter.

In an alternative mode in which information on the puncture needle is not acquired from the puncture adapter, only ID information thereof may be stored in the puncture adapter while the diameter, the insertion angle, the insertion position, or the insertion path of the puncture needle for each kind of the puncture adapter may be stored separately in the puncture needle information memory unit. In this case, a mere readout of the ID information from the puncture adapter enables specification of the diameter, the insertion angle, the insertion position, and the insertion path of the puncture needle. In a still alternative mode, the user may enter a kind of the puncture adapter to be used by means of the user input unit in lieu of storing the ID information in the puncture adapter.

Where the puncture adapter is used to determine the insertion angle, the insertion position, or the insertion path of the puncture needle or where the control line table can be produced by extraction of the puncture needle characteristics, entry of information on the puncture needle by the user need not necessarily be accepted.

The ultrasound image generating apparatus 100 may have a configuration that permits puncture both through the use of the puncture adapter and in freehand mode or permits only one of these modes.

Further, the puncture adapter may have a configuration comprising an insertion angle changing mechanism to permit selection of a stepwise variable insertion angle. In that case, the puncture adapter has a configuration wherein, for example, the puncture adapter outputs information on the present insertion angle to the ultrasound image generating apparatus 100 each time another insertion angle is selected. Even when the puncture adapter selects another insertion angle, such configuration permits focusing on a puncture needle inserted at a different insertion angle than the preceding insertion angle. Likewise, the puncture adapter may have a configuration wherein the diameter of the puncture needle that can be used with the puncture adapter is selectable. For example, a configuration permitting variation of the diameter of a usable puncture needle may be achieved by providing a configuration permitting variation of the diameter of a hole serving as a guide for the puncture needle.

Where the insertion position and the insertion path, for example, may be previously known as when the insertion path has been determined by the puncture adapter, the insertion path is preferably displayed on the monitor. Display of the insertion path on the monitor enables the user to perform puncture while viewing the insertion path on the monitor and thus prevents deviation of the puncture needle from the insertion path.

In these configurations, the probe used with the ultrasound image generating apparatus 100 is preferably exchangeable. When the probe used with the ultrasound image generating apparatus 100 is exchangeable, the user need only purchase one ultrasound image generating apparatus and can, as desired, switch between probes according to an intended use.

While this embodiment has been described by way of examples where the focus is placed on the puncture needle as imaging target in the first echo signal, the focus need not necessarily be placed on the puncture needle, and the first echo signal may be acquired by focusing on an imaging target the user desires to view. The posterior wall of a blood vessel is an example of imaging targets other than the puncture needle. When the posterior wall of a blood vessel is an imaging target, the ultrasound image is binarized to extract blood vessel representatives in order to determine the focal point position of an enhancement target image. The binarization darkens the blood vessel portions, enabling blood vessel representative points to be located. Upon locating the blood vessel representative points, the ultrasound image generating apparatus uses information such as body mark to acquire information on an imaging region, narrows down the blood vessel positions, and displays them on the monitor. Upon the user selecting a target blood vessel position from among the blood vessel representatives, the ultrasound image generating apparatus places the focal point of the ultrasonic waves for acquiring the first echo signal on the position selected by the user. Thus, even when the posterior wall of a blood vessel is an imaging target, the echo signal focused on the posterior wall of a blood vessel can be acquired.

While the focal point position in the second echo signal is placed at a fixed depth in this embodiment, the focal point position need not necessarily be fixed; the synthesized echo signal can be acquired, provided that the focal points are placed on a uniform position. Examples of such cases include a case where the depth of the focal point position gradually decreases from left to right in an image and a case where the depth of the focal point position is reduced locally. The uniform focal point position for the second echo signal may be entered by the user, or alternatively, the apparatus may have a plurality of uniform positions previously stored therein so that the user may make a selection therefrom. Also in that case, the weights for the addition of the individual images may be determined according to the focal point positions in the individual images.

While this embodiment has been described by way of examples where ultrasound signals emitted from five piezoelectric devices form a single ray sound, the invention is not limited to a configuration of ultrasound signals emitted from five piezoelectric devices forming a single ray sound, provided that the focal point position on the sound ray is controllable. For example, ultrasound signals emitted from four piezoelectric devices may form a single sound ray, or ultrasound signals emitted from seven piezoelectric devices may form a single sound ray.

Although this embodiment has a configuration permitting correction of the control line table, the control line table need not necessarily be correctable. The control line table correction function may be previously set on the system setting screen of the ultrasound image generating apparatus 100, or the input unit such as function keys may be assigned a correction function to enable ON/OFF operation at any time.

Although, the first echo signal is first acquired in this embodiment, the second echo signal may be acquired first.

Further, the first echo signal may be acquired a plurality of times to acquire a mean first echo signal and perform weighted addition of the mean first echo signal and the second echo signal, or the second echo signal may be acquired a plurality of times to acquire a mean second echo signal and perform weighted addition of the first echo signal and the mean second echo signal. The first echo signal and the second echo signal may be acquired a plurality of times to perform weighted addition of a mean first echo signal and a mean second echo signal. The mean first echo signal and the mean second echo signal may be acquired, for example, by multi-focus processing and frame mean processing. Such weighted addition using mean echo signals result in weighted addition of echo signals with a reduced speckle noise and enables reduction of the noise in the synthesized echo signal.

While the weighted addition is performed of the reception sound rays in this embodiment, the weighted addition need not necessarily be performed of the reception sound rays and may be performed of any of the data permitting weighted addition. For example, the weighted addition may be performed after the ultrasound image is produced from the reception sound rays.

Although, in this embodiment, the image memory unit for storing the images and the puncture needle memory unit for storing the puncture needles are shown as separate blocks in FIG. 1, these separate memory units need not necessarily be provided, and the images and the puncture needles may be stored in the same memory unit.

Although, in this embodiment, the CPU 104, the addition ratio calculator 118, and the weighted addition processor 120 are provided as separate blocks, the CPU 104 may be adapted to perform all the calculations.

Although, in this embodiment, the user input unit 102 is provided in the ultrasound image generating apparatus 100, the ultrasound image generating apparatus 100 need not necessarily be provided with the user input unit 102. For example, a configuration may be formed wherein the user enters input data via an external keyboard or the like.

While, in this embodiment, the weights for addition of the first echo signal and the second echo signal are provided as previously produced graphs, the user may alter the weights as desired. The weights may preferably be altered while the scan is underway by means of, for example, a weight altering knob or the touch panel of the monitor depending on which of the images the user desires to enhance for observation Although, in this embodiment, the transmitter/receiver 114, the transmission beamformer 110, and the reception beamformer 112 are provided in the ultrasound image generating apparatus 100, these units need not necessarily be provided in the ultrasound image generating apparatus 100 and may be provided in, for example, the probe 128.

While this embodiment has been described by way of examples where puncture is performed, the invention may be used for surgery or other applications where puncture is not performed.

The embodiments of the invention described above only illustrate examples of the invention and do not limit the configuration of the invention in any manner. The ultrasound image generating apparatus of the invention is not limited by the above embodiments and may be modified or implemented in various manners without departing from the spirit and scope of the invention.

The ultrasound image generating apparatus of the invention may be used to generate tomographic images of a subject using ultrasonic waves.

What is claimed is:

1. An ultrasound image generating apparatus comprising:
a transmitter/receiver which causes a probe to transmit and receive first ultrasonic waves and second ultrasonic waves,
an electronic focus controller and a CPU which controls a focal point of said first ultrasonic waves and a focal point of said second ultrasonic waves transmitted and received by said probe for each of transmission sound rays,
a weighted addition processor which performs weighted addition of a first echo signal received upon transmission of said first ultrasonic waves and a second echo signal received upon transmission of said second ultrasonic waves to obtain a synthesized echo signal,
an image display controller which generates an ultrasound image from said synthesized echo signal obtained by said weighted addition processor, and
a target information memory unit which previously stores a control line table produced from a diameter, an insertion angle, an insertion position or an insertion path of a puncture needle,
wherein said CPU determines a depth of said focal point for each of said transmission sound rays in said first ultrasonic waves based on said control line table stored in said target information memory means and said electronic focus controller controls a position of said focal point of said first ultrasonic waves so as to be located on the puncture needle and an extension of the puncture needle, which are an imaging target, and controls a position of said focal point of said second ultrasonic waves so as to be located at a same depth,
wherein said transmitter/receiver causes said probe to transmit said first ultrasonic waves and said second ultrasonic waves having said positions of said focal points controlled by said electronic focus controller and said CPU, and
said weighted addition processor determines weights to be used in said weighted addition for each of reception sound rays in said first echo signal and said second echo signal based on both a depth of said focal point for each of said transmission sound rays in said first ultrasonic waves and a depth of said focal point for each of said transmission sound rays in said second ultrasonic waves.

2. The ultrasound image generating apparatus according to claim 1, wherein said weighted addition processor changes said weights used in said weighted addition according to depths of said reception sound rays in said first echo signal and said second echo signal to undergo said weighted addition.

3. The ultrasound image generating apparatus according to claim 2, wherein said weighted addition processor smoothly changes said weights used in said weighted addition as the depths of said reception sound rays increase in a second region, which is a region between said focal point for each of said transmission sound rays in said first ultrasonic waves and said focal point for each of said transmission sound rays in said second ultrasonic waves.

4. The ultrasound image generating apparatus according to claim 3,
wherein said weighted addition processor increases a weight of said first echo signal in said weighted addition as the depth of said focal point of said first ultrasonic waves is approached, and
wherein said weighted addition processor increases a weight of said second echo signal in said weighted addition as the depth of said focal point of said second ultrasonic waves is approached.

5. The ultrasound image generating apparatus according to claim 1, wherein said electronic focus controller and said CPU correct said control line table stored in said target information memory unit by extracting characteristics of said puncture needle which is said imaging target including a diameter, an insertion angle, an insertion position or an insertion path of said puncture needle based on a differential image of said ultrasound image and fitting of said control line table and said characteristics of said puncture needle extracted, and determines a depth of said focal point for each of said transmission sound rays in said first ultrasonic waves based on a corrected control line table.

6. The ultrasound image generating apparatus according to claim 1, wherein said weighted addition processor does not perform said weighted addition in a region where a depth of said focal point for each of said transmission sound rays in said first ultrasonic waves is greater than a maximum visual field depth.

7. The ultrasound image generating apparatus according to claim 1, wherein said weighted addition processor makes the weight of said first echo signal 0 in a region where a depth of said focal point for each of said transmission sound rays in said first ultrasonic waves is greater than a maximum visual field depth.

8. The ultrasound image generating apparatus according to claim 1, wherein said electronic focus controller and said CPU places a focal point at a position shallower than a maximum visual field depth when a depth of said focal point of said first ultrasonic waves controlled by said electronic focus controller and said CPU is located at a position deeper than said maximum visual field depth.

9. The ultrasound image generating apparatus according to claim 1, wherein said weighted addition processor gradually reduces the weight of said first echo signal or said second echo signal, whichever has a deeper focal point as the depth increases in a third region located in a position deeper than the position of said focal point in said first ultrasonic waves or said focal point in said second ultrasonic wave, whichever is located in a deeper position.

10. An ultrasound image generating apparatus comprising:
probe control means for causing a probe to transmit and receive first ultrasonic waves and second ultrasonic waves,
focal point control means for controlling a focal point of said first ultrasonic waves and a focal point of said second ultrasonic waves transmitted and received by said probe for each of transmission sound rays,
weighted addition means for performing weighted addition of a first echo signal received upon transmission of said first ultrasonic waves and a second echo signal received upon transmission of said second ultrasonic waves to obtain a synthesized echo signal,
image generating means for generating an ultrasound image from said synthesized echo signal obtained by said weighted addition means, and
target information memory means for previously storing a control line table produced from a diameter, an insertion angle, an insertion position or an insertion path of a puncture needle,
wherein said focal point control means determines a depth of said focal point for each of said transmission sound rays in said first ultrasonic waves based on said control line table stored in said target information memory means and controls a position of said focal point of said first ultrasonic waves so as to be located on the puncture needle and an extension of the puncture needle, which are an imaging target, and controls a position of said focal point of said second ultrasonic waves so as to be located at a same depth, wherein said probe control means causes said probe to transmit said first ultrasonic waves and said second ultrasonic waves having said positions of said focal points controlled by said focal point control means, and said weighted addition means determines weights to be used in said weighted addition for each of reception sound rays in said first echo signal and said second echo signal based on both a depth of said focal point for each of said transmission sound rays in said first ultrasonic waves and a depth of said focal point for each of said transmission sound rays in said second ultrasonic waves.

* * * * *